United States Patent
Tabary et al.

(10) Patent No.: US 8,781,071 B2
(45) Date of Patent: Jul. 15, 2014

(54) METHOD FOR EXTRACTING A PRIMARY DIFFUSION SPECTRUM

(75) Inventors: Joachim Tabary, Grenoble (FR); Jean Rinkel, Fontaine (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 314 days.

(21) Appl. No.: 13/373,917

(22) Filed: Dec. 5, 2011

(65) Prior Publication Data
US 2012/0140891 A1 Jun. 7, 2012

(30) Foreign Application Priority Data
Dec. 6, 2010 (FR) .................................. 10 60121

(51) Int. Cl.
*G01T 1/36* (2006.01)
*G21K 1/06* (2006.01)
(52) U.S. Cl.
USPC .............................................. 378/82; 378/84
(58) Field of Classification Search
USPC ................................................ 378/70, 82, 84
See application file for complete search history.

(56) References Cited

PUBLICATIONS

Evans, B. L. et al., "Demonstration of Energy-Coded Compton Scatter Tomography with Fan Beams for One-Sided Inspection," Nuclear Instruments and Methods in Physics Research A, vol. 480, No. 2-3, 2002, pp. 797-806.
Flisch, A. et al., "Correction of Scattered Radiation for Cone-beam Computed Tomography at High X-ray Energies," Nuclear Science Symposium Record, 2008, pp. 547-554.
French Preliminary Search Report dated Sep. 14, 2011 for corresponding French Patent Application No. 1060121, 2 pages.
Thierry, R. et al., "Hybrid Simulation of Scatter Intensity in Industrial Cone-Beam Computed Tomography," Nuclear Instruments and Methods in Physics Research A, vol. 598, No. 2, 2009, pp. 611-619.

*Primary Examiner* — Irakli Kiknadze
(74) *Attorney, Agent, or Firm* — Brinks Gilson & Lione (57) ABSTRACT

A method and device for spectrometry analysis and for extracting a primary diffuse spectrum from a diffusion spectrum of diffuse radiation, according to a diffusion angle, coming from a material exposed to incident radiation through a surface, that includes the application of a spectral response function organized in the form of a matrix (M), known as a correlation matrix, of which each value $a_{ij}$ corresponds with a number of detected photons, with energy $E_i$, constituting the multiple diffuse radiation, when a photon is detected, with energy $E_j$, of the primary diffuse radiation.

13 Claims, 5 Drawing Sheets

METHOD FOR EXTRACTING A PRIMARY DIFFUSION SPECTRUM

PRIORITY CLAIM

This application claims priority to French Patent Application No. 1060121, filed Dec. 6, 2010, the entire contents of which are incorporated by reference herein.

TECHNICAL FIELD

The invention relates to a method for processing a diffuse radiation spectrum through a material exposed to incident radiation, in order to extract the primary diffuse radiation spectrum. It relates also to an associated processing device and a computer program for this processing method.

BACKGROUND

The application domain of the invention extends in the first place to the spectrometry of diffuse X rays or gamma rays, in particular the analysis of materials, but it comprises also other diffusion spectrometries. This type of spectrometry can be used in the study of materials, for instance the detection of explosives.

The diffusion spectrometry of X rays is based on exposing a material to incident X rays with energy equal to a few tens to a few hundreds keV. When they encounter the material on which they are projected, the X photons induce different types of interaction with the material: fluorescence or internal conversion (photoelectric effect during which the photon transfers all its energy to the material which returns it afterwards), inelastic diffusion, (or Compton effect which includes a change in the direction of the photon and a reduction of its energy), creation of positon-electron pairs (uniquely for X rays with very high energy not considered in the present invention), or Rayleigh diffusion (or elastic diffusion, a minority of the considered energies).

SUMMARY

The invention applies by preference to the processing of signals produced by X ray tubes delivering photons with energy between zero and 300 keV. This kind of photons diffuses in material.

Certain characteristics of the studied materials (absorption coefficient $\mu(E)$, density, ratio $$\frac{Z}{A}$$

between the atomic number Z and the atomic mass number A, and the chemical composition in particular) can in principle be determined on the basis of theoretical knowledge and by obtaining the primary diffuse spectrum of the material exposed to X rays, in other words, the diffusion spectrum which would be obtained in a situation whereby each photon is interacting only once with the material. Patent application FR 0955011, filed on Jul. 20, 2009, shows for instance how certain characteristics of the material can be determined by analyzing the energy spectrum of a diffused radiation through this material, when the latter is submitted to irradiation by X rays.

The X ray diffusion spectra comprise an important component of diffused photons that have interacted several times with the material. This component is called the multiple diffused spectrum.

Certain information, in particular the density of the material, can be obtained based on the total diffused spectrum because the attenuating character of the material affects in similar manner the two components, primary and multiple, of the diffusion spectrum. To obtain a better estimate of this density, and other physical or chemical information, it is observed that the use of the total diffusion spectrum leads to imperfect results.

PCT Application Publication No. WO2007/007247 discloses the use of a system where the studied object is placed between the radiation source and a matrix of pixellated detectors. The detector is calibrated on the basis of characteristic lines of the source, and the multiple diffusion is evaluated for each of these characteristic lines before being extrapolated to the whole spectrum.

The invention is placed in another context, because it applies in the first place to an analysis system with a strongly collimated radiation source, and a detector placed in the same half-space as the source opposite the surface of the studied material, which is also strongly collimated.

The goal of the invention is to remedy, in the context of this analytic arrangement, the problem mentioned above, by proposing a correction method for the total diffuse radiation spectrum in order to extract from it the primary diffuse radiation spectrum, in other words a radiation that diffused only once in the analyzed material before being detected.

For this purpose, a method is proposed for extracting a primary diffuse radiation spectrum from a diffuse radiation spectrum, according to a diffusion angle, coming through a material exposed to incident radiation through a surface, the method comprises the application of a spectral response function corresponding to the multiple diffuse radiation spectrum when a photon of given energy is detected belonging to the primary diffusion spectrum, said spectral response function is organized in the form of a matrix (M), called correlation matrix, of which each value $a_{ij}$ corresponds to the number of detected photons, with energy $E_j$, constituting the multiple diffuse radiation, when a photon with energy $E_j$ is detected, of the primary diffuse radiation. Thanks to this method, the primary diffuse spectrum is easily extracted and access is gained to extensive physical-chemical information. Furthermore, this matrix calculation mode offers the advantage of efficiency, specifically in terms of programming.

According to one aspect of the invention, the spectral response function provides a discretized spectrum over a finite number of energy bands.

According to one advantageous aspect of the invention, the method comprises an iterative process in which each step comprises an estimation of the multiple diffusion spectrum after a preceding estimation of the primary diffuse spectrum, and a new estimation of the primary diffusion spectrum, by subtracting said estimated multiple diffusion spectrum from the detected diffusion spectrum, said iterative process is continued until a convergence criterion is satisfied related to the successive estimated primary diffuse spectra, or, as a variant, until a predetermined number of iterations is executed.

According to one implementation mode, the spectral response function is the result of interpolating a plurality of spectral response spectra with monochromatic exposure of the different materials for the given depth, taking into account only the density of the material.

According to another implementation mode, the spectral response function is the result of interpolating a plurality of spectral response functions of the material, for different depths.

It is also proposed that the spectral response function is obtained beforehand by experimental acquisition of a response of the material for the given depth.

According to one aspect of the invention, the method includes also a preliminary step consisting of estimating a first spectrum of estimated primary diffusion, by multiplying a measured total diffusion spectrum with a multiplication coefficient dependent on the inspection depth.

The invention consists also of a device for extracting a primary diffuse radiation spectrum from a diffusion spectrum of a radiation diffused through a material to be analyzed, the device comprises an incident source of radiation suitable for irradiating a surface of the material to be analyzed, a detector suitable for detecting the radiation diffused through said material according to at least one preselected diffusion angle, and means for applying a spectral response function corresponding to the multiple diffused radiation spectrum when a photon is detected with given energy belonging to the primary diffusion spectrum, said spectral response function is organized in the form of a matrix (M), called correlation matrix, of which each value $a_{ij}$ corresponds with a number of detected photons, with energy $E_i$, constituting the multiple diffuse radiation, when a photon is detected, with energy $E_j$, of the primary diffuse radiation.

Advantageously and according to the invention, the radiation source and detector are both strongly collimated. On the other hand, in a variant combination, the detector is by preference placed in the same half-space as the radiation source opposite the irradiated surface of the material to be analyzed.

The invention extends also to a spectrometry analysis device comprising such device for extracting the first diffuse radiation spectrum.

The invention is also proposing a computer program comprising a sequence of instructions suitable, when executed by a microprocessor, for executing a method according to the invention.

BRIEF DESCRIPTION OF THE DRAWING

The invention will now be described in relation to the attached figures, representing non-limiting illustrations.

DETAILED DESCRIPTION

Figure 1:
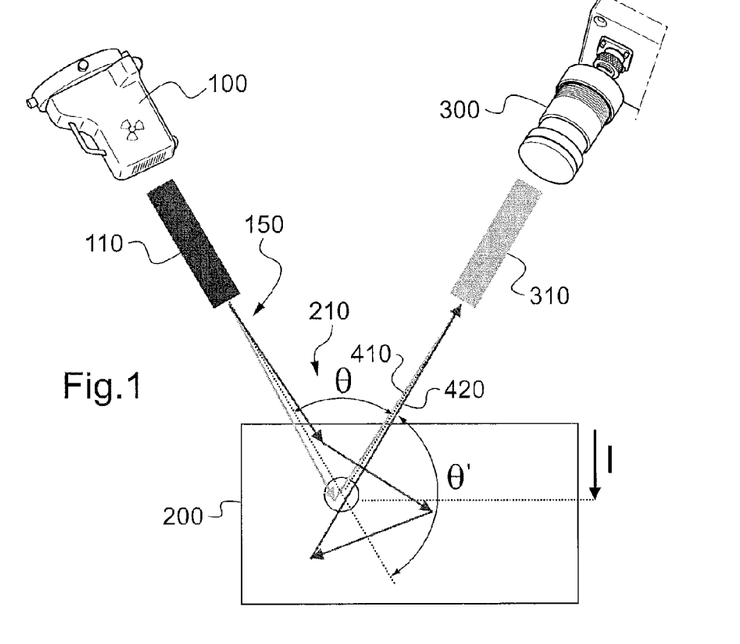
FIG. 1 represents an implementation mode of the device according to the invention.

FIG. 1 shows the equipment arrangement employed in a method according to the invention. A source 100 emits a radiation X 150 which is collimated by a collimator 110. The radiation 150 forms a beam with very small opening angle, typically a few degrees, around the central axis of the source collimator. The source 100 is mono energetic, or poly energetic, and emits photons in continuous manner over a whole energy range. The beam is projected on a material volume 200 through a surface 210 of the material.

The photons X interact with the material according to various physical phenomena mentioned in the introduction. Certain photons interact very close to the surface, while others penetrate deep into the material. A detector 300 equipped with a collimator 310 observes the surface 210 of the material 200 and measures the energy of the photons which it is able to receive thanks to its collimation angle.

The positioning relative to source 100 and detector 300 and their placement opposite material 200 and their respective collimation angles define an analysis depth in the material 200, which is such that the photons measured by the detector 300 originate from a volume of material 200 called inspection volume. This volume is determined by the intersection between the solid angles according to which the source and the detector see the material volume 200. The respective collimation axes of source and detector intersect in the analyzed material. The analysis depth, or inspection depth, corresponds to the distance between the material surface and this intersection. The detector detects the photons emitted by the source and diffused according to an angle $\theta'=\pi-\theta$ in the inspection volume. When $\theta'=0$, there is no inelastic diffusion: the photon follows a rectilinear trajectory.

Since source 100 and detector 300 are installed on the same side of surface 210, we are speaking of rear diffusion spectrum or retrodiffusion spectrum.

Figure 2:
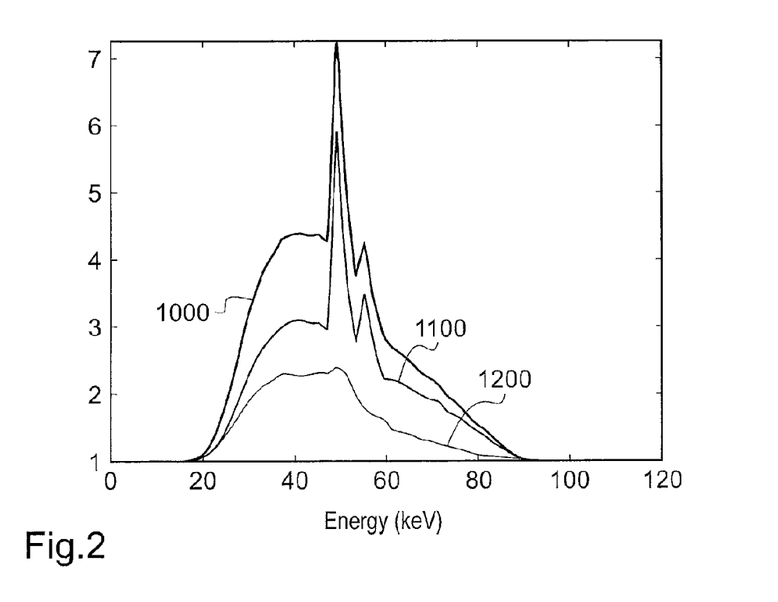
FIG. 2 shows the general decomposition of diffusion spectra.

FIG. 2 shows the diffusion spectrum measured for a given material 200. The x-axis represents the energy of the photons which extends typically from 20 to 100 keV, and the y axis represents the intensity of the detected radiation for a given energy in arbitrary unit. The total diffusion spectrum 1000 is decomposed in a primary diffusion spectrum 1100 and a multiple diffusion spectrum 1200 as mentioned in the introduction.

FIG. 1 shows the trajectory of a primary diffusion photon 410. By definition, its trajectory changes only once: it is diffused only once before reaching the detector. The diffusion takes place according to the diffusion angle $\theta'$, and occurs in the inspection volume. Just like the previously mentioned photon, these photons form the primary diffusion radiation according to angle $\theta'$, constituted of photons diffused only once, according to this diffusion angle $\theta'$, in the inspection volume.

The trajectory is also represented of a multiple diffusion photon which was the object of various interactions with the material 200 and which changes trajectory at each of these interactions. It undergoes multiple diffusions before reaching the detector. We speak then of multiple diffuse radiation, because the radiation is constituted of photons having diffused more than once before reaching the detector.

To be noted that also other photons come from the material volume 200, like photons 410 and 420, at other angles and are not measured by the detector 300. Therefore, they do not appear on the spectra of FIG. 2.

A portion of the primary diffuse radiation and the multiple diffuse radiation is detected by the detector. The detector is not capable of distinguishing between these two components. The detector measures the energy of the radiation spectrum, of the total diffuse radiation, noted DT. The latter is composed of a component corresponding to the primary diffusion spectrum, noted DP, previously defined and a component corresponding to the multiple diffusion spectrum, noted DM, previously defined.

The total diffusion spectrum is the sum of the primary diffusion spectrum and the multiple diffusion spectrum.

$$DT=DP+DM$$

Figure 3:
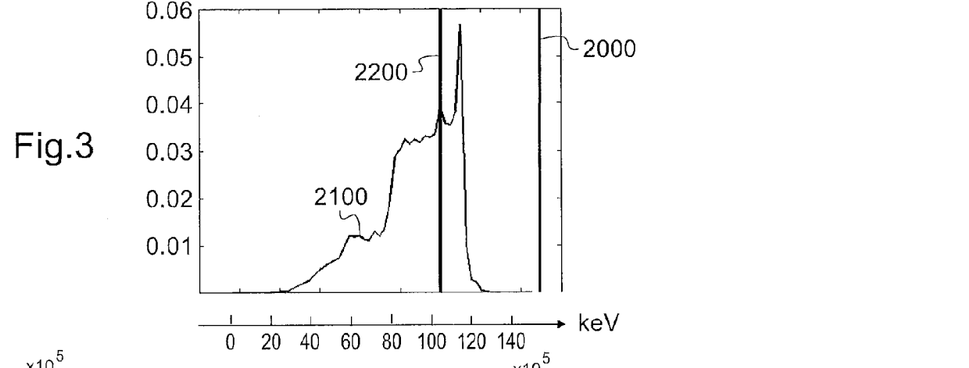
FIG. 3 shows the spectral response to monochromatic exposure of a material as envisioned in the invention.

FIG. 3 shows the spectral response of the diffuse radiation in reaction to monochromatic exposure of material 200 in the arrangement of FIG. 1. The material used for the example is Delrin (registered trademark) and the monochromatic excitation 2000 is performed at 150 keV. The inspection volume is at a depth of 4 cm, the angle between the incident beam and the collimation axis of the detector is 120°. As expected, it is observed that the spectral response 2100 is composed uniquely of energies smaller than the monochromatic excitation energy 2000.

In an analysis system as shown in FIG. 1, in other words using retrodiffusion, measurement and collimation both of the source and the detector, the primary diffuse spectrum in response to a monochromatic excitation is linked in objective manner to the activation energy, and is in essence monochromatic. It is indicated by reference 2200 in FIG. 3.

Outside the energy measured in close proximity of an energy value corresponding to the whole primary diffusion spectrum 2200, which in FIG. 3 is 104.14 keV, the whole diffusion spectrum 2100 is constituted of the multiple diffuse component DM.

This spectrum DM is represented in discretized form on a limited number n of energy detection channels, by column vector $$\begin{pmatrix} a_1 \\ a_j \\ ... \\ a_n \end{pmatrix},$$

where $a_j$ is the intensity of the multiple diffuse radiation at energy $E_j$. The vector depends naturally of the material and the analysis depth.

The material can be irradiated according to a large number of monochromatic energies $E_{irradiation-i}$, each energy $E_{irradiation-i}$ being such that the primary diffuse radiation, according to angle θ', detected by the detector has energy $E_i$. The totality of the responses of the material to monochromatic excitations, discretized for a specific number of energy detection channels is represented in the form of a correlation matrix.

$$M = \begin{pmatrix} a_{11} & a_{1j} & ... & a_{1p} \\ a_{i1} & a_{ij} & ... & ... \\ ... & ... & ... & ... \\ a_{n1} & ... & ... & a_{np} \end{pmatrix}$$

In this matrix, each value $a_{ij}$ corresponds to the proportion of detected photons constituting the multiple diffuse radiation, with energy $E_i$ when a photon is detected, with energy $E_j$, of the primary diffuse radiation.

In this manner, each sum of coefficients $a_{ij}$ according to a column j of this matrix corresponds to the number of detected multiple diffused photons $N_{multiples-j}$ when a primary diffuse photon with energy $E_j$ is detected.

$$N_{multiples-j} = \sum_i a_{i,j}$$

Each column $C_j$ of matrix M represents the energy spectrum of the multiple diffuse radiation detected when a primary diffuse photon with energy $E_j$ is detected. This function is called spectral response function and corresponds to the detection of a primary diffuse photon with energy $E_j$.

The method according to the invention is using the correlation matrix M to extract in iterative manner the component of the multiple diffusions in the experimentally measured diffusion spectrum. It involves an iterative process, allowing for an estimation of the primary diffusion spectrum DP. With each iteration k, an estimate is made of the primary diffusion spectrum, noted $DP_k$. This estimate is made by using the previously defined correlation matrix, according to the following algorithm:

$$DM_k=M*DP_{k-1} \quad (1)$$

$$DP_k=DT-DM_k \quad (2)$$

where:
$DM_k$: estimate of the multiple diffusion spectrum during iteration k;
$DP_{k-1}$: estimate of the primary diffuse spectrum established at iteration k−1 when k≠1. Exceptionally, when k=1, $DP_{k-1}$ is the initial estimate of the primary diffusion spectrum;
DT: total diffusion spectrum, in other words diffusion spectrum measured by the detector.

The iterations continue either according to a predetermined number of iterations, or until a convergence criterion is reached, as described below.

The iterative process comprises
an initial estimate of the primary diffuse spectrum (initialization stage)
estimation of the multiple diffusion spectrum $DM_k$ corresponding to the primary diffusion spectrum of the preceding iteration $DP_{k-1}$ or, during the primary iteration, of the initial estimation of the primary diffuse spectrum ($DP_0$). This estimation is done by means of the correlation matrix M.
a new estimation of the primary diffusion spectrum $DP_k$, performed by subtracting the estimated multiple diffuse spectrum $DM_k$ from the measured diffusion spectrum DT,
a new iteration step during which the multiple diffuse spectrum is evaluated on the basis of the estimation of the primary diffuse spectrum.

According to the method of fixed point inversion, the two components are separated in the physically measured spectrum.

The initial primary diffuse spectrum, indicated by $DP_{k=0}$ is initially estimated on the simple basis of the measured total diffusion spectrum DT, multiplied by a global attenuation factor, indicated by α, between 0.3 and 1 in function of the inspection depth, for materials with density between 0.7 and 2.2. For an inspection depth of 2 cm, a value of 0.6 is used, and for an inspection depth of 4 cm, the value is 0.45. These values can be adjusted with each start up.

In this way, $$DP_{k=0}=\alpha DT$$

Knowing the total diffuse spectrum DT (this is the spectrum measured by the detector), and the initial estimation value of the primary diffuse spectrum $DP_{k=0}$, the previously described steps (1) and (2) are completed, in iterative manner, until the convergence criterion is achieved or until the number of iterations reaches the predetermined number.

A possible convergence criterion is the distance between the successive estimates of the two primary diffusion spectra, $DP_{k-1}$ and $DP_k$, this distance can be expressed as follows $$\|DP_k - DP_{k-1}\| = \sqrt{\sum_E (DP_k(E) - DP_{k-1}(E))^2} \leq \varepsilon \quad (4)$$

In this expression, the term E designates the energy and the term $\varepsilon$ designates the convergence criterion.

In each iteration the primary diffuse spectrum is represented in the form of a vector $$\begin{pmatrix} dp_1 \\ dp_2 \\ \ldots \\ dp_p \end{pmatrix}_k,$$

and the multiple diffuse spectrum is represented also in the form of a vector $$\begin{pmatrix} dm_1 \\ dm_2 \\ \ldots \\ dm_n \end{pmatrix}_k.$$

The latter is deduced through matrix calculation by the operation $$\begin{pmatrix} dm_1 \\ dm_2 \\ \ldots \\ dm_n \end{pmatrix}_k = \begin{pmatrix} a_{11} & a_{12} & \ldots & a_{1p} \\ a_{21} & a_{22} & \ldots & \ldots \\ \ldots & \ldots & \ldots & \ldots \\ a_{n1} & \ldots & \ldots & a_{np} \end{pmatrix} \cdot \begin{pmatrix} dp_1 \\ dp_2 \\ \ldots \\ dp_p \end{pmatrix}_{k-1}.$$

The energy discretization step and the dimensions of the previously described vectors are by preference identical. Also, the number of discretization channels n of the multiple diffusion spectrum is, by preference, selected equal to the number of channels p of the primary diffusion spectrum, In this case the matrix M is square.

Figure 4:
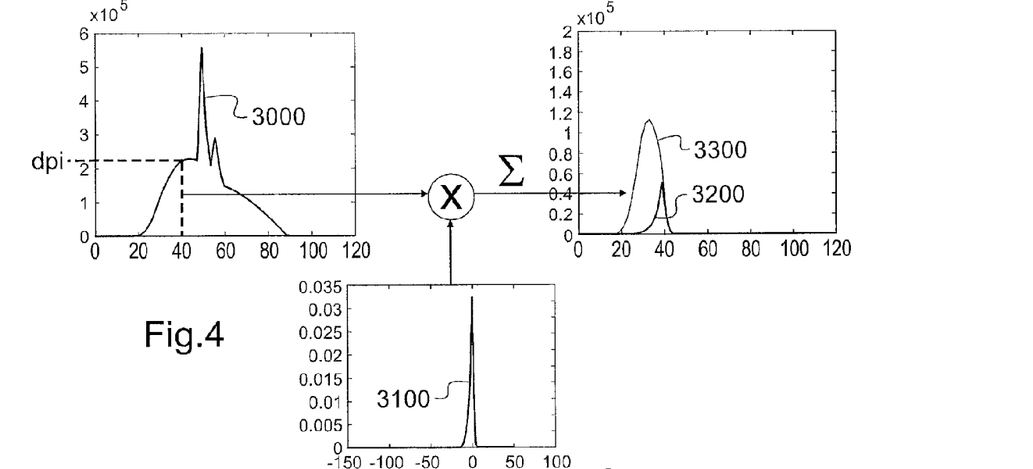
FIG. 4 shows one step of the implementation mode of a method according to the invention.
Figure 5:
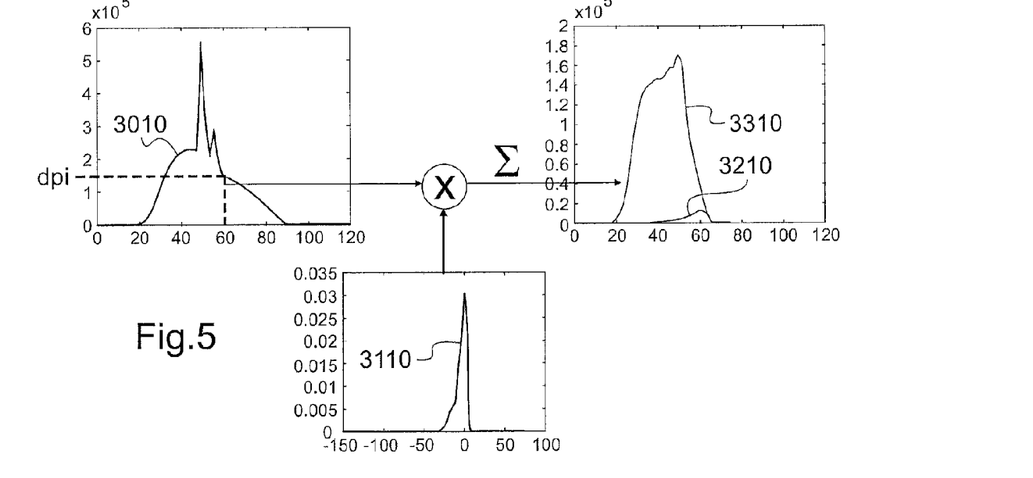
FIG. 5 shows a further step of the same method.

The iterative process is illustrated in FIGS. 4 and 5. FIG. 4 represents the multiplication of an intensity dpi of the estimated primary diffuse spectrum 3000 with energy i=40 keV with a column $a_{ij}$, where j varies from 1 to n, represented by the reference 3100 in the lower part of the figure, the result being a fraction 3200 of the estimated multiple diffuse spectrum 3300, visible on the right side of FIG. 4 and expressed in the form of a vector $$\begin{pmatrix} dm_1 \\ dm_2 \\ \ldots \\ dm_n \end{pmatrix},$$

which is added to the spectrum fractions calculated for energy values smaller than i to obtain an intermediate total 3300.

FIG. 5 shows the multiplication of another intensity $dp_i$ of the primary diffuse spectrum with energy i with a column $a_{ij}$, referenced 3110, the result is a second fraction of the estimated multiple diffuse spectrum 3210, the different fractions are then added to obtain the estimated multiple diffuse spectrum 3300.

An important element of the invention is the use of the correlation matrix M, allowing for the estimation of the multiple diffusion spectrum $DM_k$ corresponding to a given primary diffusion spectrum $DP_k$. This matrix must be established for a specific position of the source and the detector, relative to the analyzed object. Furthermore, the matrix depends of the following parameters:

the angle $\theta$ between the collimation axes of detector and source, which conditions the diffusion angle $\theta'(\theta=\pi-\theta)$
the nature of the material constituting the analyzed object
the depth of the inspection volume, which is determined by the intersection of the collimation axes of the detector and the source.

Figure 6:
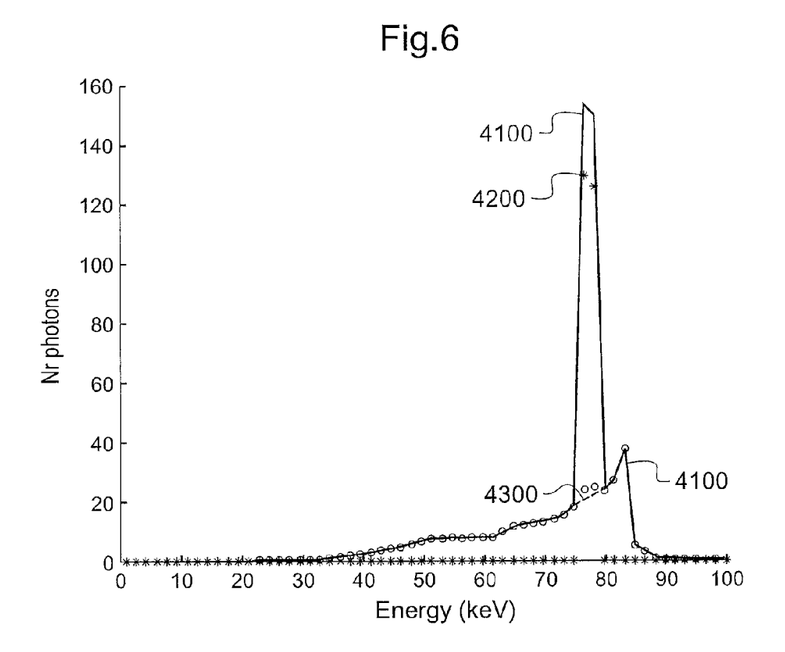
FIG. 6 shows a step of a first specific implementation mode of the invention.

Correlation matrix M can be constructed experimentally, by successive use of different sources of mono energetic X rays or gamma rays with energy $E_{irradiation-j}$, as radioactive sources with known radiation, or a synchrotron radiation, which in addition has the advantage of having great energy. The total diffusion spectrum is then measured, such as the spectrum shown in FIG. 6, and referenced 4000. The method proceeds then in three steps:

First, the primary diffusion peak is determined. Starting from the total diffusion spectrum 4100, the peak 4200 is isolated corresponding to the detected primary diffused radiation. This peak extends on both sides of a known energy, $E_j$ corresponding to the diffusion energy $E_{irradiation-j}$ of the monochromatic radiation emitted by the source according to the diffusion angle $\theta'$. This peak is finer the more the source and the detector are collimated. By preference, the half-height width of this peak corresponds to an energetic band smaller than a few keV. This peak 4200 corresponds with the primary diffusion radiation component in the detected total diffusion spectrum.

During a second step, the multiple diffuse spectrum is determined. By eliminating the primary diffusion component 4200 from the total diffusion spectrum 4100, the multiple diffusion spectrum 4300 is obtained. To this end, the "under the peak" bottom is determined, in other words the continuous curve, for instance a linear curve, joining the two extremities of the 4300 spectrum from both sides of the basis of the peak 4200. Algorithms for determining the signal under a peak can be used, which are currently employed in the domain of X ray or gamma ray spectrometry.

Finally, during a third step, the normalization takes place. The multiple diffusion spectrum 4300 is divided by the quantity of photons corresponding to the primary diffusion peak 4200. The multiple diffusion spectrum normalized in this manner corresponds then to the multiple diffusion spectrum obtained when a photon of primary diffuse radiation is detected. This spectrum corresponds also to a column $C_j$ of the correlation matrix M, of which the index j corresponds with the energy $E_j$ of the observed primary diffusion peak, the latter is determined by the energy $E_{irradiation-j}$ of the radiation source and the diffusion angle $\theta'$.

The three described steps can be performed by simulation instead of experimentally, for instance by using a Monte Carlo type code for particle transport known to a person skilled in the art, and in particular MCNP, GEANT or PENELOPE. Furthermore, the correlation matrix can be constituted by combining simulation and experimentation.

Renewing this operation by successively using, or simulating, different mono energetic sources, it is possible to obtain several columns of the matrix, corresponding to as many primary diffusion energies $E_j$, the latter are calculated after knowing the diffusion angle θ' and the emission energy $E_{irradiation-j}$ of the source employed. These different columns can be interpolated among them, for instance in linear manner, in order to construct a complete matrix, the energy discretization step between each row and each column corresponding respectively to the energy discretization step of the vector representing a multiple diffusion spectrum and to the energy discretization step of the vector representing the primary diffusion spectrum.

Such a matrix is created for different measurement configurations, by varying the following parameters:
  the nature of the sample material
  position, in the sample material, of the intersection of the collimation axes of detector and source, this position corresponds to the inspection depth.

In this way, for a given diffusion angle, a plurality of correlation matrices M (nature, depth) is obtained.

For instance, when the diffusion angle θ' is 120°, corresponding to an angle separating the collimation axes θ of 60°, the multiple diffusion spectrum can be simulated corresponding to a mono energetic source with energy varying between 10 and 150 keV, per 10 keV step. Fifteen simulations are then necessary. This corresponds to primary diffusion photons with energy between 9.7 keV (when the energy of the source is equal to 10 keV) and 104.14 keV (when the energy of the source is equal to 150 keV). The matrix is then completed by interpolation.

These matrices are constructed for different sample materials, which can be polyethylene, water, Plexiglass (registered trademark), nylon (registered trademark), Delrin, cellulose, Kynar (registered trademark), ammonium nitrate or Teflon (registered trademark). For each material, a correlation matrix is determined for each inspection depth, the latter varying for instance between 0 and 7 cm, in steps of 0.5 cm.

For the same material, matrices can also be interpolated according to the depth.

Figure 7:
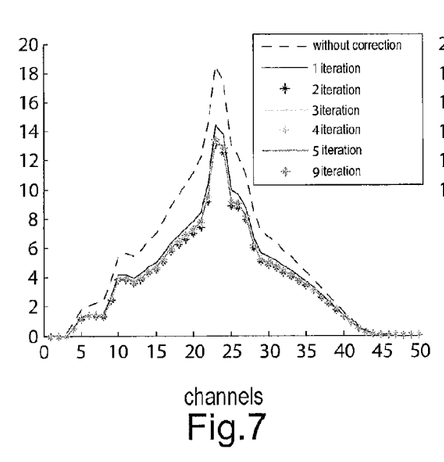
FIGS. 7 and 8 show the results obtained with the first specific implementation mode of the invention.

FIG. 7 shows an implementation example of the iterative method for estimating the primary diffusion spectrum, previously described, using plexiglass material and a depth of 2 cm. Excellent convergence of this estimation is observed. The convergence is estimated here by calculating a normalized distance between two successive estimated primary diffuse spectra and comparison between this distance and a threshold value ε according to an equation of the type $$\|DP_k - DP_{k-1}\| = \sqrt{\sum_E (DP_k(E) - DP_{k-1}(E))^2} \le \varepsilon$$

The value is reached after 5 iterations.

Figure 8:
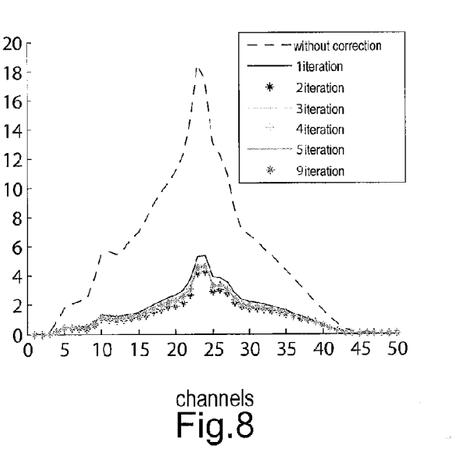

FIG. 8 shows also the convergence of the estimated primary diffuse spectrum for plexiglass studied at 4 cm depth. We observe good convergence regardless of the importance of the multiple diffusion relative to the primary diffusion.

Materials to be explored which are not listed in the pre-established data base are the object of an interpolation, for determining their correlation matrix, starting from the matrices constituting this base, according to their density. The object of the interpolation is each coefficient of the correlation matrix M, and can be a linear interpolation.

The results obtained with this approximation are excellent, because in the analytic system of FIG. 1, it is determined experimentally that the spectral distribution of the multiple diffusion for an energy of incident radiation does not depend on the material, which allows for limiting the study of the materials to their density, which determines the attenuation over the whole spectral range, for the preparation of the correlation matrix.

Figure 9:
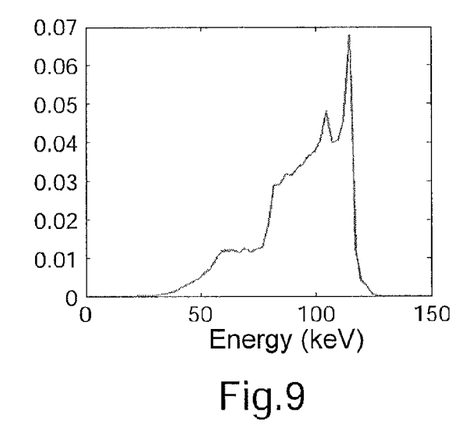
FIG. 9 shows two functions implemented in a second specific implementation mode of the invention.
Figure 10:
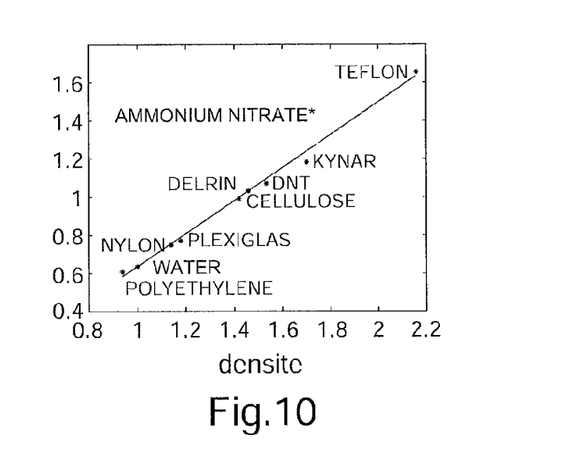
FIG. 10 shows results obtained with the second specific implementation mode of the invention.

FIG. 9 shows the spectral distribution of the multiple diffusion for a primary diffusion at 104.14 keV, which does not depend on the material and FIG. 10 shows the attenuation function for the same energy value of primary diffusion.

Interpolations can also be made for the values of the incident energy and the depth, in order to effectively adapt the used matrix M to the precise values of the studied situations.

The spectrum processing method described in this application can be applied to an unknown material, but of known or estimated density. An already constructed matrix is selected, corresponding to a material with a density close to the density of the unknown material. The extraction of the primary diffusion spectrum allows for more precise determination of the nature of this material, for instance by following the method described in patent application FR 09 55011, filed on Jul. 20, 2009, previously mentioned. It is then possible to repeat an extraction of the primary diffusion spectrum by means of a matrix taking into account the precise nature of the material, as it was previously determined.

Figure 11:
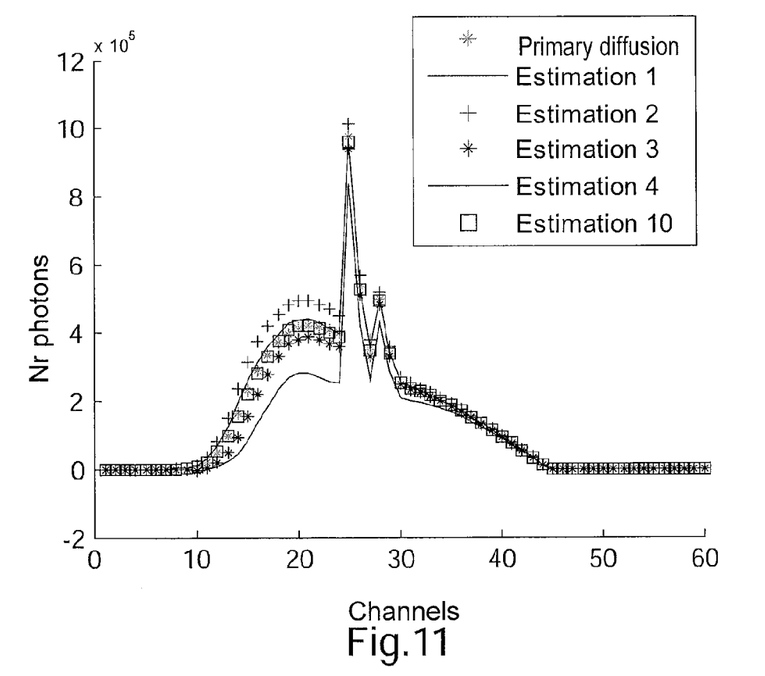
FIG. 11 shows a comparison of results obtained with the method according to the invention and measurements obtained elsewhere.

FIG. 11 shows the excellent convergence observed when determining the primary diffusion spectrum in this implementation mode, in the case a volume of plexiglass is studied at 3 cm depth. Convergence is reached in less than 10 iterations, with an oscillation phenomenon around the final spectrum.

Figure 12:
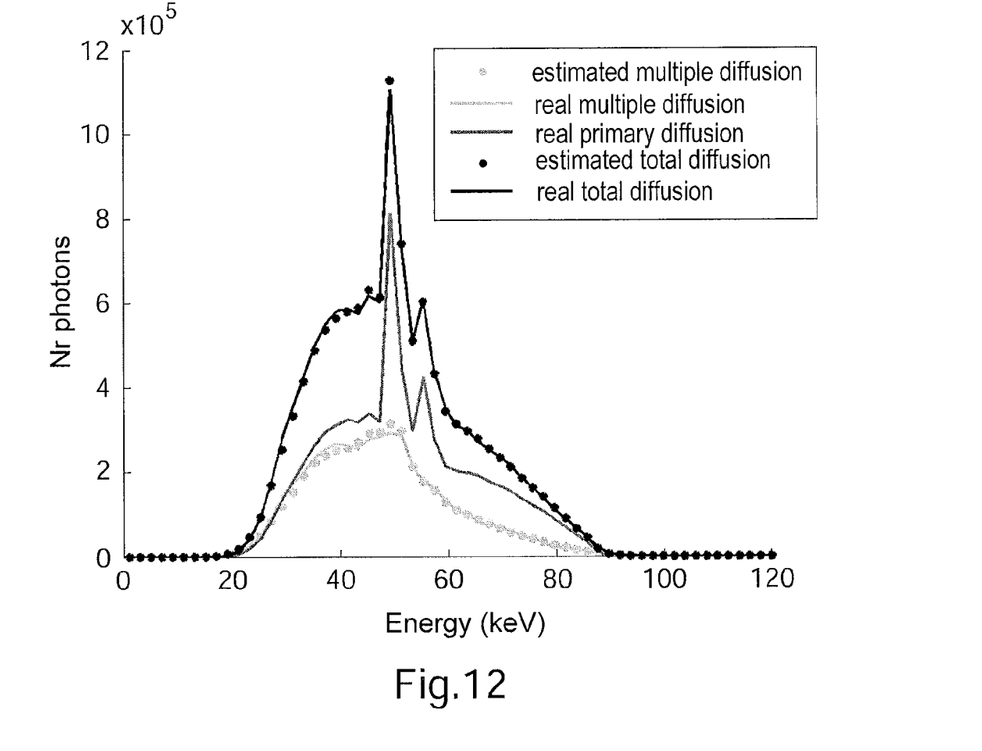
FIG. 12 shows the results of the decomposition in primary diffusion and multiple diffusion of a total diffusion spectrum obtained with Delrin studied at 3 cm depth.

FIG. 12 shows the results of the decomposition in primary diffusion and multiple diffusion of a total diffusion spectrum obtained with Delrin studied at 3 cm depth. The results are compared with simulated data of the total diffusion spectrum, the primary diffusion spectrum, and the multiple diffusion spectrum.

The invention is not limited to the described implementation mode but extends to all variants within the reach of a person skilled in the art.

The invention claimed is:

1. A method for extracting a primary diffuse radiation spectrum from a diffusion spectrum of diffuse radiation, according to a diffusion angle, coming from a material exposed to incident radiation through a surface, the method comprising:
    application of a spectral response function corresponding to a multiple diffuse radiation spectrum when a photon with a given energy belonging to the primary diffuse spectrum is detected,
    wherein the spectral response function comprises a correlation matrix (M) of which each value aij corresponds to a number of detected photons, with energy Ei, constituting the multiple diffuse radiation, when a photon of the primary diffuse spectrum is detected with energy Ej.

2. The method according to claim 1, wherein the spectral response function supplies a discretized spectrum over a finite number of energy ranges.

3. The method according to claim 1 further comprising an iterative process in which each step includes an estimation of the multiple diffusion spectrum to create an estimated multiple diffusion spectrum following a preceding estimation of the primary diffuse radiation spectrum and a new estimation of the primary diffuse radiation spectrum, by subtracting the estimated multiple diffusion spectrum from the diffusion spectrum, wherein the iterative process is continued until satisfaction of a convergence criterion related to successive estimated primary diffusion spectra.

4. The method according to claim 1, wherein the spectral response function comprises a result of interpolating a plurality of spectral response functions to monochromatic exposure of different materials for a given depth considering only the density of the different materials.

5. The method according to claim 1, wherein the spectral response function comprises a result of interpolating a plurality of spectral response functions to monochromatic exposure of the material for different depths.

6. The method according to claim 1, wherein the spectral response function is obtained beforehand by experimental acquisition of a response to monochromatic exposure of the material for a given depth.

7. The method according to claim 1 further comprising a preliminary estimation of a first estimated primary diffuse spectrum, carried out by multiplying a measured total diffusion spectrum by a multiplication coefficient dependent of the inspection depth.

8. The method according to claim 1, wherein the radiation comprises X rays.

9. A device for extracting a primary diffuse radiation spectrum from a diffusion spectrum of a diffuse radiation through a material to be analyzed, the device comprising:

a source of incident radiation configured to irradiate a surface of the material;

a detector configured to detect the radiation diffused by the material according to at least one preselected diffusion angle; and means for applying a spectral response function corresponding to a multiple diffuse radiation spectrum when a photon is detected with given energy belonging to the primary diffuse radiation spectrum, wherein the spectral response function comprises a correlation matrix (M) of which each value $a_{ij}$ corresponds with a number of detected photons, with energy $E_i$, constituting the multiple diffuse radiation, when a photon of the primary diffuse radiation is detected with energy $E_j$.

10. The device according to claim 9, wherein the radiation source and the detector are both strongly collimated.

11. The device according to claim 9, wherein the detector resides in a same half-space as the radiation source opposite the irradiated surface of the material.

12. A device for spectrometry analysis comprising a device for extracting a spectrum of primary diffuse radiation according to claim 9.

13. A non-transitory computer readable media including a sequence of instructions that, when executed by a microprocessor, implement the method according to claim 1.

* * * * *